(12) United States Patent
Huang et al.

(10) Patent No.: US 11,751,819 B2
(45) Date of Patent: Sep. 12, 2023

(54) ALARM SYSTEM FOR MONITORING PHYSICAL DISORDER OF USER DURING IMMERSIVE VR EXPERIENCE

(71) Applicant: FOSHAN JIEPIN TOY INDUSTRIAL CO., LTD., Foshan (CN)

(72) Inventors: Zhi Huang, Foshan (CN); Zhenjiang Qu, Foshan (CN)

(73) Assignee: FOSHAN JIEPIN TOY INDUSTRIAL CO., LTD., Foshan (CN)

( * ) Notice: Subject to any disclaimer, the term of this patent is extended or adjusted under 35 U.S.C. 154(b) by 0 days.

(21) Appl. No.: 17/717,147

(22) Filed: Apr. 11, 2022

(65) Prior Publication Data
US 2022/0233153 A1  Jul. 28, 2022

(51) Int. Cl.
| | |
|---|---|
| *A61B 5/00* | (2006.01) |
| *G08B 21/18* | (2006.01) |
| *G08B 21/02* | (2006.01) |
| *G06T 19/00* | (2011.01) |

(52) U.S. Cl.
CPC ............ *A61B 5/746* (2013.01); *G06T 19/00* (2013.01); *G08B 21/02* (2013.01); *G08B 21/182* (2013.01)

(58) Field of Classification Search
CPC ........ A61B 5/746; G06T 19/00; G08B 21/02; G08B 21/182
USPC ..................................................... 340/573.1
See application file for complete search history.

(56) References Cited

U.S. PATENT DOCUMENTS

| | | | |
|---|---|---|---|
| 10,231,662 B1* | 3/2019 | Berme | G06F 3/0334 |
| 10,242,713 B2* | 3/2019 | Rothschild | G16H 40/63 |
| 2012/0108909 A1* | 5/2012 | Slobounov | A61B 5/16 600/300 |
| 2015/0198446 A1* | 7/2015 | Perez | G06Q 20/1085 705/43 |
| 2016/0077547 A1* | 3/2016 | Aimone | A61B 5/1114 345/8 |
| 2016/0166153 A1* | 6/2016 | Woo | A61B 5/14552 600/324 |
| 2016/0183880 A1* | 6/2016 | Abe | A61B 5/721 600/301 |
| 2017/0323485 A1* | 11/2017 | Samec | A61B 5/14532 |
| 2019/0057584 A1* | 2/2019 | Brayton | G08B 1/08 |
| 2019/0142287 A1* | 5/2019 | Böscke | A61B 5/02427 600/479 |

(Continued)

*Primary Examiner* — Zhen Y Wu

(57) ABSTRACT

The present invention provides an alarm system for monitoring a physical disorder of a user during an immersive virtual reality (VR) experience. The alarm system includes a physical information monitoring module, a control module, a display module, an alarm module, and a power module. The control module is configured to receive the human body physical sign information transmitted by the physical information monitoring module and feed back the information to the display module and the alarm module. When a user wearing a VR device has an adverse physical response during an experience and use, the alarm system of the present invention can quickly transmit a corresponding warning and prompt according to a detected abnormal physical sign. If the user has an adverse physical response and cannot carry out self-help, a remote call for help can be quickly made through software, thereby providing maximum protection for the user.

6 Claims, 2 Drawing Sheets

(56) References Cited

U.S. PATENT DOCUMENTS

| | | | |
|---|---|---|---|
| 2019/0160286 A1* | 5/2019 | Yang | A61N 1/36025 |
| 2019/0232113 A1* | 8/2019 | Zets | A61B 5/1128 |
| 2019/0290193 A1* | 9/2019 | Hayik | A61B 5/002 |

* cited by examiner

ALARM SYSTEM FOR MONITORING PHYSICAL DISORDER OF USER DURING IMMERSIVE VR EXPERIENCE

TECHNICAL FIELD

The present invention relates to the field of virtual reality (VR) devices, and in particular to, an alarm system for monitoring a physical disorder of a user during an immersive VR experience.

BACKGROUND

VR technology is a technology that creates a simulated three-dimensional scene through a computer system to cater to a human body to provide a multi-sensory, multi-dimensional experience. With the update, iteration, and rapid development of the VR technology, a user can have a more realistic experience and enjoy an immersive experience for an increasingly long time. The user can feel a very realistic virtual environment when wearing VR glasses or another head-mounted display device, to generate an immersive VR experience.

When a user wears a VR device, the user is detached from the real surroundings and the user's vision and hearing of the real surroundings are completely blocked, making the user almost completely isolated from the real outside world.

When a user wears a VR device for experiencing, the user feels scene screen content with the eyes, and may see intensive and intense content very similar to real-life content. The visual experience transmitted through the retinas may make the user's optic nerve, brain, and other organs of the body produce real responses. Such content (for example, violent, frightening, sentimental or adrenaline-inducing content) may trigger an increased heart rate, increased blood pressure, mental fear, panic, loss of balance, post-traumatic stress disorder, vertigo or other adverse side effects, or even worse, may induce vertigo, convulsions, seizures, loss of consciousness, muscle twitching, coma or even cardiac arrest.

Hardware manufacturers or software developers of VR products only provide cautions in the description, which may not subjectively remind and protect a user adequately.

There is a need for a novel VR device alarm system with a monitoring and early warning system, so that when a user wears a VR device and has an adverse physical response during an experience, a corresponding warning and prompt can be quickly transmitted to the user according to a detected abnormal physical sign. When the user has an adverse physical response, the user can be warned, or a remote call can be quickly made when the user falls into coma or the user's vital signs are extremely abnormal, thereby protecting the user.

SUMMARY

The present invention provides an alarm system for monitoring a physical disorder of a user during an immersive VR experience. When a user wearing a VR device has an adverse physical response during an experience and use, a corresponding warning and prompt can be quickly pushed to the user according to a detected abnormal physical sign. If the user falls into a coma or has another adverse physical response and cannot carry out self-help, a preset function in software can be used to quickly make a remote call for help, thereby providing maximum protection for the user.

To achieve the foregoing objective, the technical solutions adopted in the present invention are as follows.

An alarm system for monitoring a physical disorder of a user during an immersive VR experience, including a physical information monitoring module, a control module, a display module, an alarm module, and a power module. The physical information monitoring module, the control module, the display module, and the alarm module are electrically connected to the power module. The physical information monitoring module is configured to monitor human body physical sign information. The control module is configured to receive the human body physical sign information transmitted by the physical information monitoring module and feed back the human body physical sign information to the display module and the alarm module. The display module is connected to the alarm module and a VR device host.

Preferably, the physical information monitoring module includes an LED photoelectric chip component, a reflection photosensitive sensor, an optical heart rate sensor, and a contact temperature sensor. The physical information monitoring module is disposed at a wrist, an arm or a temple of a human body.

Preferably, the LED photoelectric chip component emits a light wave with a wavelength of 525 nm.

Preferably, the human body physical sign information includes information of a breathing rate, blood pressure, a blood oxygen level, a heart rate, and body temperature data of a human body.

Preferably, the power module is a lithium-ion battery.

Preferably, an information storage module, a data analysis module, and a data transmission module are disposed in the control module. A human body physical sign model is set in the information storage module. The control module receives human body monitoring data transmitted by the physical information monitoring module and stores the human body monitoring data in the information storage module. The data analysis module compares the human body monitoring data with the human body physical sign model set in the information storage module. A plurality of monitoring data exception levels are further set in the data analysis module. The control module is connected to the display module and the alarm module by the data transmission module.

Preferably, the alarm module includes an audio player and a video player. The audio player and the video player are connected to the VR device host by the display module. The alarm module presets different audio or videos according to different monitoring data exception levels for playback.

Preferably, the alarm module further includes a wireless module and a remote control terminal. The wireless module is disposed on the control module, and the control module is wirelessly connected to the remote control terminal by the wireless module. An automatic alert module is disposed in the remote control terminal. The control module has a preset monitoring data threshold. After the human body physical sign information transmitted by the physical information monitoring module reaches the monitoring data threshold, the automatic alert module can automatically raise an alert and transmit distress information preset in the remote control terminal.

Preferably, the wireless module is a Bluetooth transmission chip, a Wi-Fi transmission chip, and a Global Positioning System receiver chip.

The present invention has the follow beneficial effects.

The physical information monitoring module of the present invention is a modular device formed by a plurality of sensors. The device includes a reflection photosensitive sensor, an optical heart rate sensor, a contact temperature sensor, and an LED photoelectric chip component.

A user may wear the module on the wrist, arm or temple. A built-in LED emits a light wave with a wavelength of 525 nm into skin. The light wave penetrates skin tissue. Scattered light of light reflected by blood flow is measured, and is received by the photosensitive sensor and converted into an electrical signal, which is in turn converted into a digital signal. An input of a photoplethysmography (PPG) algorithm is used to capture the breathing rate, blood pressure, blood oxygen level, and heart rate of a wearer. The temperature sensor captures the body temperature data of the wearer. All the captured data is stored in an information storage module, and is compared with a human body physical sign model set in the information storage module by a data analysis module. The worn device monitors the blood pressure, heart rate, blood oxygen level, and temperature of the user, and displays related information on a display device of a display module.

When the user has a physical disorder, the alarm module plays different audio or videos preset according to different monitoring data exception levels to transmit a prompt and an alert.

A wireless module and a remote control terminal are further disposed in the present invention. After the human body physical sign information transmitted by the physical information monitoring module reaches a monitoring data threshold, an automatic alert module can automatically raise an alert and transmit distress information preset in the remote control terminal, to automatically make a remote call for help.

When the user wearing a VR device has an adverse physical response during an experience and use, the alarm system of the present invention can quickly transmit a corresponding warning and prompt to the user according to a detected abnormal physical sign. If the user falls into coma or has another adverse physical response and cannot carry out self-help, a preset function in software can be used to quickly make a remote call for help, thereby providing maximum protection for the user.

Figure 1:
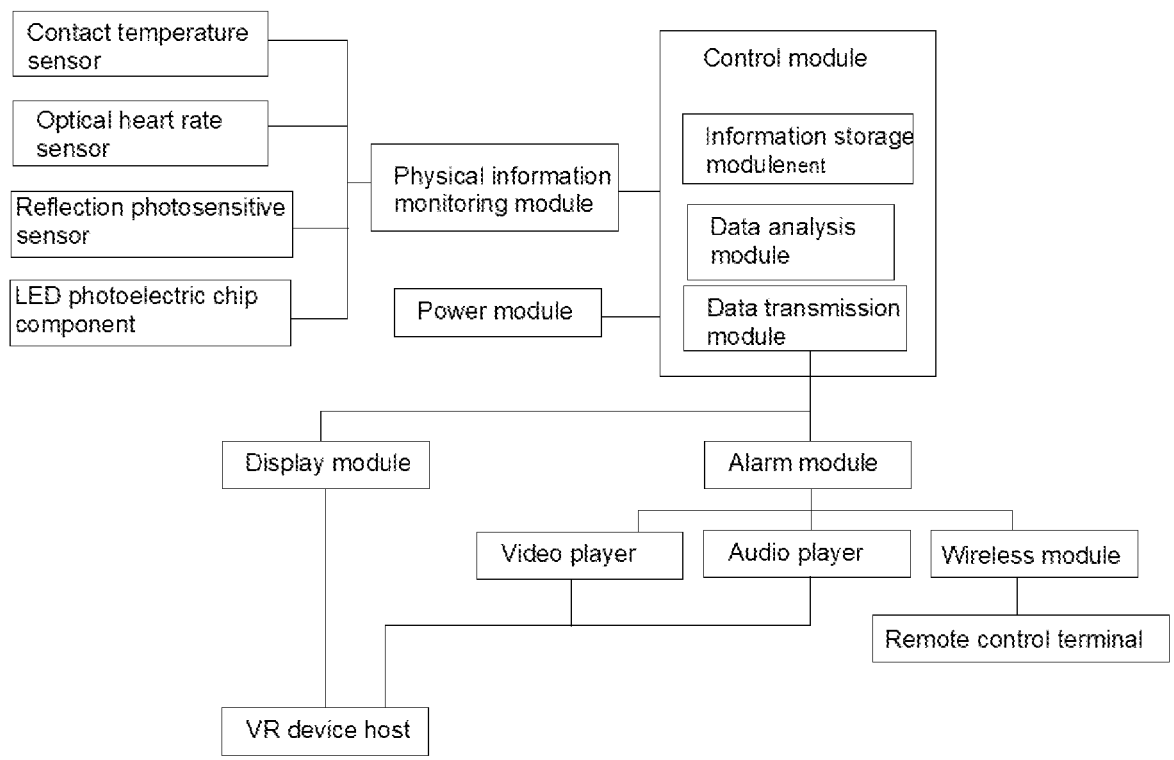
FIG. 1 is a schematic diagram of modular connections according to the present invention.

Reference numerals: temple position 1, arm position 2, wrist position 3, and physical information monitoring module 4.

DETAILED DESCRIPTION

Figure 2:
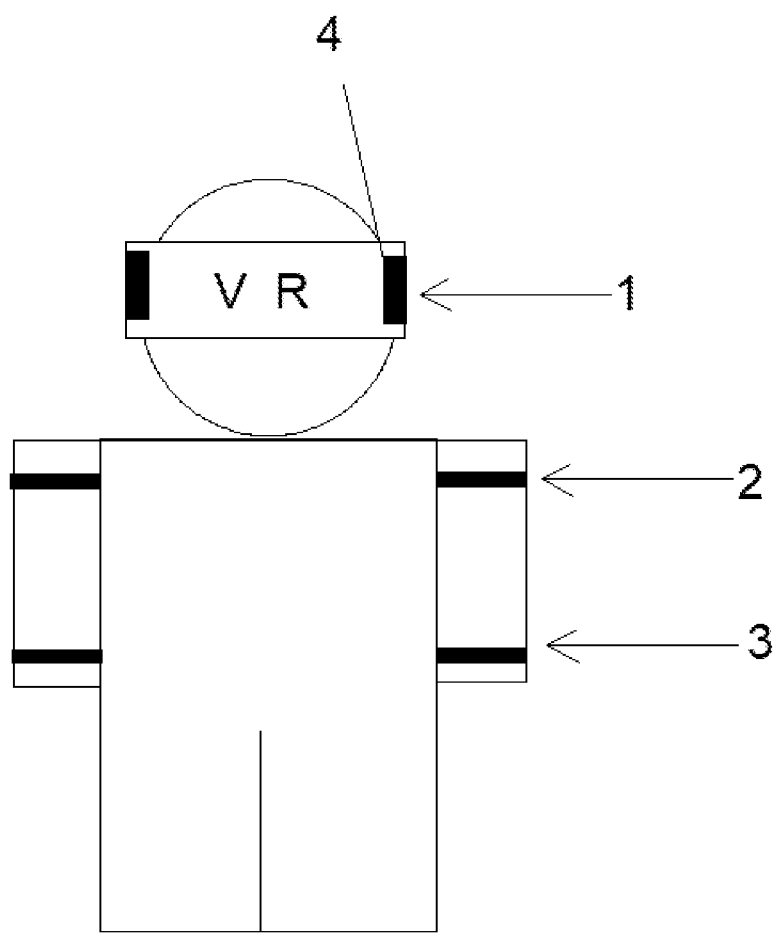
FIG. 2 is a schematic diagram of a mounting position of a physical information monitoring module according to the present invention.

Referring to FIG. 1 and FIG. 2, the present invention provides an alarm system for monitoring a physical disorder of a user during an immersive VR experience, including a physical information monitoring module, a control module, a display module, an alarm module, and a power module. The physical information monitoring module, the control module, the display module, and the alarm module are electrically connected to the power module. The physical information monitoring module is configured to monitor human body physical sign information. The control module is configured to receive the human body physical sign information transmitted by the physical information monitoring module and feed back the human body physical sign information to the display module and the alarm module. The display module is connected to the alarm module and a VR device host.

Further, in order to enable the physical information monitoring module to acquire data of the human body physical sign information, the physical information monitoring module includes an LED photoelectric chip component, a reflection photosensitive sensor, an optical heart rate sensor, and a contact temperature sensor. The physical information monitoring module is disposed at a wrist, an arm or a temple of a human body. The reflection photosensitive sensor and the optical heart rate sensor can monitor a breathing rate, blood pressure, a blood oxygen level, and a heart rate of the human body, and the temperature sensor can acquire the body temperature data of a wearer.

As shown in FIG. 2, a physical information monitoring module 4 is disposed at a temple position 1, an arm position 2 or a wrist position 3.

Further, the LED photoelectric chip component emits a light wave with a wavelength of 525 nm. A built-in green LED emits a light wave with a wavelength of 525 nm. The green LED is used because its light wave has high penetrating power and can be easily absorbed by hemoglobin. The light wave with a wavelength of 525 nm of the LED enters skin. Light reflected by skin tissue is received by a photosensitive sensor.

Further, the human body physical sign information includes a breathing rate, blood pressure, a blood oxygen level, a heart rate, and body temperature data of a human body.

Further, in order to obtain a rechargeable power module and improve the battery life, the power module adopts a lithium-ion battery.

Further, an information storage module, a data analysis module, and a data transmission module are disposed in the control module. A human body physical sign model is set in the information storage module. The control module receives human body monitoring data transmitted by the physical information monitoring module and stores the human body monitoring data in the information storage module. The data analysis module compares the human body monitoring data with the human body physical sign model set in the information storage module. A plurality of monitoring data exception levels are further set in the data analysis module. The control module is connected to the display module and the alarm module by the data transmission module.

Further, the alarm module includes an audio player and a video player. The audio player and the video player are connected to the VR device host by the display module. The alarm module presets different audio or videos according to different monitoring data exception levels for playback. A warning and a prompt are pushed to a screen of the VR device host.

Further, the alarm module further includes a wireless module and a remote control terminal. The wireless module is disposed on the control module, and the control module is wirelessly connected to the remote control terminal by the wireless module. An automatic alert module is disposed in the remote control terminal. The control module has a preset monitoring data threshold. After the human body physical sign information transmitted by the physical information monitoring module reaches the monitoring data threshold, the automatic alert module can automatically raise an alert and transmit distress information preset in the remote control terminal.

Further, the wireless module is a Bluetooth transmission chip, a Wi-Fi transmission chip, and a Global Positioning System receiver chip.

The control module and the remote control terminal are both used as receive ends to receive the human body physical sign information transmitted by the physical information monitoring module. An alert is raised by means of the monitoring data exception levels preset in the control module, to remind a user in time that the user has a physical disorder, so that maximum protection can be provided for the user.

The embodiments have the following characteristics:
1) The physical information monitoring module in the embodiment is a modular device formed by a plurality of sensors. The device includes a reflection photosensitive sensor, an optical heart rate sensor, a contact temperature sensor, and an LED photoelectric chip component.
2) A user may wear the module at a wrist, an arm or a temple. A built-in LED emits a light wave with a wavelength of 525 nm into skin and the light wave penetrates skin tissue. Reflected light is received by the photosensitive sensor and converted into an electrical signal, which is in turn converted into a digital signal. An input of a PPG algorithm is used to capture the breathing rate, blood pressure, blood oxygen level, and heart rate of a wearer. The temperature sensor captures the body temperature data of the wearer. All the captured data is stored in an information storage module, and is compared with a human body physical sign model set in the information storage module by a data analysis module. The worn device monitors the blood pressure, heart rate, blood oxygen level, and temperature of the user, and displays related information on a display device of a display module.
3) When the user has a physical disorder, the alarm module plays different audio or videos preset according to different monitoring data exception levels to transmit a prompt and an alert.
4) A wireless module and a remote control terminal are further disposed in the embodiment. After the human body physical sign information transmitted by the physical information monitoring module reaches a monitoring data threshold, an automatic alert module can automatically raise an alert and transmit distress information preset in the remote control terminal, to automatically make a remote call for help.
5) When the user wearing a VR device has an adverse physical response during an experience and use, the alarm system of the present invention can quickly transmit a corresponding warning and prompt to the user according to a detected abnormal physical sign. If the user falls into coma or has another adverse physical response and cannot carry out self-help, a preset function in software can be used to quickly make a remote call for help, thereby providing maximum protection for the user.

Finally, it should be noted that the foregoing embodiments are merely intended for describing the technical solutions of the present invention rather than limiting the present invention. Although the present invention is described in detail with reference to the preferred embodiments, persons of ordinary skill in the art should understand that they may still make modifications or equivalent replacements to the technical features of the present invention without departing from the objective and scope of the technical solutions of the present invention. These modifications or equivalent replacements shall all fall within the scope of the claims of the present invention.

The standard parts used in the present invention are all commercially available, and the irregular parts can be customized according to the description and drawings. Mature conventional methods such as bolts, rivets, and welding in the prior art adopted for the specific connection methods of all parts. Conventional models in the prior art are adopted for all the machines, parts, and equipment. Conventional connection methods in the prior art are adopted for circuit connection. Details are not described herein in detail.

In the description of the present invention, unless otherwise expressly specified and defined, "mounted", "connected", "connection", and "fixed" should be understood in a broad sense, for example, fixedly connected, detachably connected or integrally connected; or mechanically connected or electrically connected; or connected directly or through an intermediate, or two elements communicated internally or two elements having mutual effects. For persons skilled in the art, specific meanings of the terms in the present invention should be understood according to specific conditions.

The invention claimed is:

1. An alarm system for monitoring a physical disorder of a user during an immersive virtual reality (VR) experience, comprising a physical information monitoring module, a control module, a display module, an alarm module, and a power module, wherein the physical information monitoring module, the control module, the display module, and the alarm module are electrically connected to the power module, the physical information monitoring module is configured to monitor human body physical sign information, the control module is configured to receive the human body physical sign information transmitted by the physical information monitoring module and feedback the human body physical sign information to the display module and the alarm module, and the display module is connected to the alarm module and a VR device host;

wherein the physical information monitoring module comprises a light emitting diode (LED) photoelectric chip component, a reflection photosensitive sensor, an optical heart rate sensor, and a contact temperature sensor, and the physical information monitoring module is disposed at a wrist, an arm or a temple of a human body;

wherein the alarm module comprises an audio player and a video player, the audio player and the video player are connected to the VR device host by the display module, and the alarm module presets different audio or videos according to different monitoring data exception levels for playback;

wherein the alarm module further comprises a wireless module and a remote control terminal, the wireless module is disposed on the control module, the control module is wirelessly connected to the remote control terminal by the wireless module, an automatic alert module is disposed in the remote control terminal, the control module has a preset monitoring data threshold, and after the human body physical sign information transmitted by the physical information monitoring module reaches the monitoring data threshold, the automatic alert module can automatically raise an alert and transmit distress information preset in the remote control terminal.

2. The alarm system for monitoring a physical disorder of a user during an immersive VR experience according to claim 1, wherein the LED photoelectric chip component emits a light wave with a wavelength of 525 nanometer (nm).

3. The alarm system for monitoring a physical disorder of a user during an immersive VR experience according to claim 1, wherein the human body physical sign information comprises a breathing rate, blood pressure, a blood oxygen level, a heart rate, and body temperature data of a human body.

4. The alarm system for monitoring a physical disorder of a user during an immersive VR experience according to claim 1, wherein the power module is a lithium-ion battery.

5. The alarm system for monitoring a physical disorder of a user during an immersive VR experience according to claim 1, wherein an information storage module, a data analysis module, and a data transmission module are disposed in the control module, a human body physical sign model is set in the information storage module, the control module receives human body monitoring data transmitted by the physical information monitoring module and stores the human body monitoring data in the information storage module, the data analysis module compares the human body monitoring data with the human body physical sign model set in the information storage module, a plurality of monitoring data exception levels are further set in the data analysis module, and the control module is connected to the display module and the alarm module by the data transmission module.

6. The alarm system for monitoring a physical disorder of a user during an immersive VR experience according to claim 1, wherein the wireless module is a Bluetooth transmission chip, a Wi-Fi transmission chip, and a Global Positioning System receiver chip.

\* \* \* \* \*